United States Patent [19]

Fields, Jr. et al.

[11] Patent Number: 5,061,820

[45] Date of Patent: Oct. 29, 1991

[54] PROCESS FOR PRODUCING N-PHOSPHONOMETHYLGYLCINE

[75] Inventors: Donald L. Fields, Jr., Manchester; Raymond C. Grabiak, Maryland Heights; Karl E. Koenig; Dennis P. Riley, both of Ballwin, all of Mo.

[73] Assignee: Monsanto Company, St. Louis, Mo.

[21] Appl. No.: 600,954

[22] Filed: Oct. 22, 1990

[51] Int. Cl.$^5$ .............................................. C07F 9/38
[52] U.S. Cl. ...................................................... 560/17
[58] Field of Search ........................................... 562/17

[56] References Cited

U.S. PATENT DOCUMENTS 3,954,848   5/1976   Franz .............................. 260/502.5
4,952,723   8/1990   Fields et al. ........................ 562/17
4,983,764   1/1991   Pelyva et al. ....................... 562/17

FOREIGN PATENT DOCUMENTS 20356     12/1981   Hungary .
187347    5/1988    Hungary .
2049697   12/1980   United Kingdom .................. 562/17

Primary Examiner—J. E. Evans
Attorney, Agent, or Firm—Frank D. Shearin

[57] ABSTRACT

A process for the production of N-phosphonomethylglycine comprising contacting N-phosphonomethyliminodiacetic acid with a peroxide in the presence of a catalyst selected from the group consisting of the salts and salt complexes of cobalt and vancadium, and an effective amount of dipyridyl compound.

17 Claims, No Drawings

PROCESS FOR PRODUCING N-PHOSPHONOMETHYLGYLCINE

BACKGROUND OF THE INVENTION

This invention relates to a process for preparing N-phosphonomethylglycine by the oxidation of N-phosphonomethyliminodiacetic acid using a peroxide and a homogeneous catalyst system. More particularly, this invention relates to a process for producing N-phosphonomethylglycine by the peroxide oxidation of N-phosphonomethyliminodiacetic acid using a salt of a selected metal in the presence of a dipyridyl compound.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-Phosphonomethylglycine and its salts are conveniently applied in an aqueous formulation as a postemergent phytotoxicant for the control of numerous plant species. N-Phosphonomethylglycine and its salts are characterized by broad spectrum activity, i.e., the controlled growth of a wide variety of plants.

Numerous methods are known in the art for the oxidation of the N-phosphonomethyliminodiacetic acid to N-phosphonomethylglycine. For example, U.S. Pat. No. 4,952,723 to Fields, et al. discloses a process for the production of N-phosphonomethylglycine by contacting N-phosphonomethyliminodiacetic acid with a molecular oxygen-containing gas in the presence of a catalyst selected from the group consisting of the salts and salt complexes of manganese, cobalt, iron, nickel, chromium, ruthenium, aluminum, molybdenum, vanadium and cerium, and an effective amount of a dipyridyl compound. There is no suggestion, however, that peroxides could be used instead of the molecular oxygen-containing gas.

U.S. Pat. No. 3,954,848 to Franz discloses a process for the production of N-phosphonomethylglycine by reacting N-phosphonomethyiminodiacetic acid with an oxidizing agent, such as hydrogen peroxide, in an aqueous acidic medium in the presence of a strong acid at a temperature of from about 70° C. to about 100° C. It is disclosed that one should employ at least 2 moles of the hydrogen peroxide for each mole of the N-phosphonomethyliminodiacetic acid, and preferably more.

Hungarian Patent Application No. 187,347 discloses a process for the preparation of N-phosphonomethylglycine by the oxidation of N-phosphonomethyliminodiacetic acid with peroxides using a catalytic amount of a metal compound selected from compounds of silver, iron, tin, lead, manganese or molybdenum. Molybdates are preferred. At temperatures lower than 80° C., usually a contaminated end product is obtained. Typically, the reaction is carried out at a temperature of above 80° C. and preferably about 100° C. at pressure exceeding atmospheric. It is further disclosed that at least two mole equivalents of peroxide should be used for each mole equivalent of N-phosphonomethyliminodiacetic acid.

Although satisfactory results are obtained by the above processes to make N-phosphonomethylglycine, all of them suffer from one or more disadvantages, such as the use of excessive amounts of peroxide, and/or reaction at elevated temperatures and pressures. Now, there is disclosed a process which provides N-phosphonomethylglycine in high yields at modest temperatures and at atmospheric pressure.

SUMMARY OF THE INVENTION

These and other advantages are achieved by a process for the production of N-phosphonomethylglycine comprising contacting N-phosphonomethyliminodiacetic acid with a peroxide in the presence of a catalyst selected from the group consisting of the salts and salt complexes of cobalt and vanadium, and an effective amount of a dipyridyl compound represented by the formula

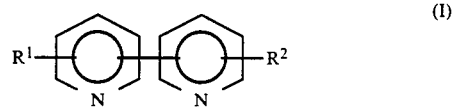

(I)

wherein $R^1$ and $R^2$ are independently selected from the group consisting of hydrogen, alkyl having from one to about 18 carbon atoms, ortho-phenylene, oxygen, sulfur, $SO_2$, $SO_3$, $N-R^5$ wherein $R^5$ is alkyl having from one to six carbon atoms, and $R^1$ and $R^2$ together can form a bridge with groups selected from alkylene having from one to about six carbon atoms; wherein the alkylene bridge can contain branching or double bonds; or salts thereof represented by the formula

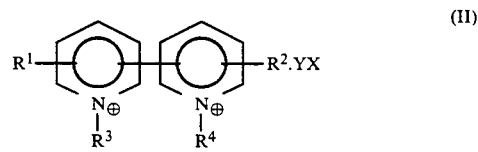

(II)

wherein $R^1$ and $R^2$ are as defined above, Y is one or two depending on whether X is a dianion or a monoanion, and X is selected from the group consisting of halide, sulfate and nitrate, phosphate, perchlorate, and the like; and $R^3$ and $R^4$ are individually selected from the group consisting of hydrogen or alkyl having from one to about 18 carbon atoms, and $R^3$ and $R^4$ together can form a bridge with groups selected from alkylene having from one to about six carbon atoms wherein the alkylene bridge can contain branching or double bonds.

DETAILED DESCRIPTION OF THE INVENTION

The process of the present invention involves contacting N-phosphonomethyliminodiacetic acid with a salt or a salt complex of selected metals in a mixture or solution. The mixture or solution is contacted with a peroxide while heating the reaction mass to a temperature sufficiently high to initiate and sustain the oxidation reaction of N-phosphonomethyliminodiacetic acid to produce N-phosphonomethylglycine.

The catalyst in the present invention can be any one or more of the salt and salt complexes of cobalt or vanadium. Suitable salts include cobalt sulfate, cobalt(II or III) acetylacetonate, cobalt chloride, cobalt bromide, cobalt nitrate, cobalt acetate, vanadium sulfate, vanadium bromide, vanadium chloride, and the like.

The catalyst can be added to the N-phosphonomethyliminodiacetic acid in the salt form, or the salt may be generated in situ by the addition of a source of the metal ion, such as vanadium pentoxide which dissolves in the reaction mixture.

The concentration of the catalyst in the process of the present invention can vary within wide limits. The concentration can vary between about 1 molar to about 0.000 molar total metal ion concentration. For most of the metal salts, the reaction appears to have a first order dependency on the catalyst concentration, i.e., the reaction rate increases linearly as a catalyst concentration increases. The preferred concentration for the catalyst metal ion is in the range of about 0.1 molar to about 0.001 molar which gives a suitably fast rate of reaction that can be easily controlled and favors selectivity to N-phosphonomethylglycine.

Of the metal catalyst salts that can be used in the process of the present invention, the salt and salt complexes of cobalt or vanadium can be used, and especially beneficial are the bromide and sulfate salts of cobalt and vanadium. Vanadium salts are especially preferred, and of these, vanadyl sulfate is the most preferred.

The dipyridyl compounds of the present invention are known to the art, and can be represented by the formula

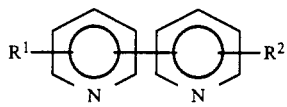

(I)

wherein $R^1$ and $R^2$ are independently selected from the group consisting of hydrogen, alkyl having from one to about 18 carbon atoms, ortho-phenylene, oxygen, sulfur, $SO_x$, $N-R^5$ wherein $R^5$ is alkyl having from one to six carbon atoms, and $R^1$ and $R^2$ together can form a bridge with groups selected from alkylene having from one to about six carbon atoms, wherein the alkylene bridge can contain branching or double bonds.

When $R^1$ and $R^2$ form a bridge, the compounds can be represented by formulas such as

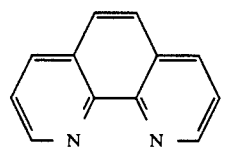

(III)

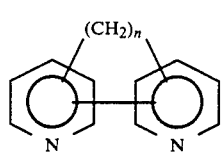

(IV)

where n is from one to about 18.

The salts of the dipyridyl compounds can be used and can be represented by the formula:

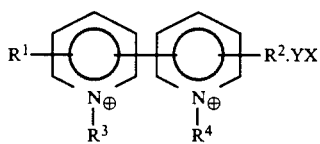

(II)

wherein $R^1$ and $R^2$ are as defined above, Y is one or two depending on whether X is a dianion or a monoanion and X is selected from the group consisting of halide, sulfate and nitrate, phosphate, perchlorate, and the like; and $R^3$ and $R^4$ are individually selected from the group consisting of hydrogen or alkyl having from one to about 18 carbon atoms, and $R^3$ and $R^4$ together can form a bridge with groups selected from alkylene having from one to about six carbon atoms wherein the alkylene bridge can contain branching or double bonds.

When $R^3$ and $R^4$ form a bridge, the dipyridyl compounds can be represented by the formula:

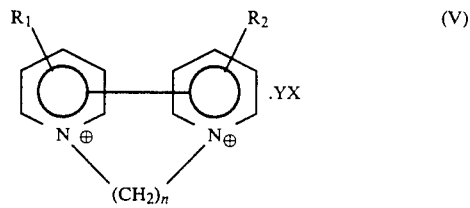

(V)

where n is from one to about 18. It should be noted, however, that the free bases of the 2,2-dipyridyl compounds are not as effective as the other isomers in the process of the present invention due to its rate inhibiting effects.

The compounds represented by Formula II where $R^3$ and $R^4$ are each methyl and X is chloride and Y is 2 are preferred, but especially preferred are the compounds of Formula V wherein X is bromide and n and Y are 2.

The concentration of the dipyridyl compound in the process of the present invention can vary within wide limits, depending upon the catalyst salt that is used and the particular dipyridyl compound that is selected. In general, it has been found that the concentration of the dipyridyl compound can vary from about 0.01 molar in the reaction solution to 0.5 molar, and higher concentrations of the dipyridyl compound can be used, although such higher concentrations do not seem to have a significant effect on the oxidation rate of N-phosphonomethyliminodiacetic acid to N-phosphonomethylglycine. It has been found that concentrations of the dipyridyl compound between about 0.1 molar to about 0.5 molar provides satisfactory results, and this is the concentration that is preferred.

The temperature of the process to prepare the N-phosphonomethylglycine can vary from as low as about 20° C. to about 100° C. Although temperatures below about 20° C. can be used, such temperatures would require the use of cooling, and no advantages are obtained. At temperatures above about 100° C., degradation is observed, which affects the final yield of the desire N-phosphonomethylglycine. Temperatures between about 20° C. and about 85° C. are preferred.

To carry out the process of the present invention, it is only necessary to bring N-phosphonomethyliminodiacetic acid together with an effective amount of the catalyst salt and an effective amount of the dipyridyl compound in the presence of a peroxide. Any number of peroxides known to those skilled in the art can be used in the process of the present invention. Suitable peroxides include hydrogen peroxide, performic acid, peracetic acid, perbenzoic acid, peroxytrifluoroacetic acid, benzoyl peroxide, benzenepersulfonic acid, and the like. Hydrogen peroxide is preferred, and it is advantageous to the use hydrogen peroxide in the form of a concentrated solution, say between about 30% and 60%.

In the process of the present invention, the amount of peroxide should be twice the stoichiometric amount required to convert the N-phosphonomethyliminodiacetic acid to N-phosphonomethylglycine. As will occur to those skilled in the art, when less than twice the stoichiometric amount of peroxide is used, the yield of the desired N-phosphonomethylglycine is lower. A slight excess of peroxide can be used to insure a quantitative conversion of the N-phosphonomethyliminodiacetic acid, but there is no advantage to using large excesses of peroxide, and excesses of peroxide may be deleterious.

As will occur in those skilled in the art in view of the presence disclosure, the manner in which the solution or mixture of N-phosphonomethyliminodiacetic acid is contacted with the peroxide in the presence of the metal salt catalyst and the dipyridyl compound can vary greatly. For example, the N-phosphonomethyliminodiacetic acid solution can be contacted with the peroxide with agitation, such as bubbling, stirring, shaking, and the like. The process of the present invention only requires actively contacting the peroxide with the aqueous solution or mixture of N-phosphonomethyliminodiacetic acid containing the metal catalyst salt and the dipyridyl compound.

The initial pH of the reaction affects the reaction rate and the selectivity to N-phosphonomethylglycine. The initial pH of the reaction can vary between about pH 0.1 to about pH 7. A preferred range is from about pH 0.1 to pH 3, and a more preferred pH range is the undiluted pH of the N-phosphonomethyliminodiacetic acid in an aqueous solution which varies with the N-phosphonomethyliminodiacetic acid concentration and the reaction temperature.

The oxidation reaction can take place in a solution or a slurry. For a solution the initial concentration of the N-phosphonomethyliminodiacetic acid in the reaction mass is a function of the solubility of the N-phosphonomethyliminodiacetic acid is the solvent (i.e., water) at both the desired reaction temperature and the initial pH of the solution. As the solvent temperature and the initial pH changes, the solubility of N-phosphonomethyliminodiacetic acid changes. It has been found that the process of the present invention works with very dilute solutions or even with a slurry of the N-phosphonomethyliminodiacetic acid in an aqueous solution. The reaction is typically carried out in an aqueous solvent, i.e., containing at least about 50 wt.% water. The preferred aqueous solvent is distilled, deionized water.

The invention is further illustrated by, but not limited to, the following examples. The percent selectivity to N-phosphonomethylglycine was determined by dividing the moles of N-phosphonomethylglycine and N-formyl-N-phosphonomethylglycine produced by the total moles of N-phosphonomethyliminodiacetic acid consumed and multiplying by 100. The percent conversion of N-phosphonomethyliminodiacetic acid was determined by dividing the moles of N-phosphonomethyliminodiacetic acid that was reacted by the total moles of starting N-phosphonomethyliminodiacetic acid and multiplying by 100.

EXAMPLES 1-5

Into a 100 ml round-bottomed flask was charged N-phosphonomethyliminodiacetic acid (13.5 g, 0.06 mol) vanadyl sulfate (0.5 g), water (50 g) and 0.003 mole of the additive. The mixture was heated to 80° C., and 30% hydrogen peroxide (17.5 g) was added dropwise over a 30-minute period. The temperature was kept below 85° C. by the addition rate of hydrogen peroxide. Heating was continued at 85° C. until the solution turned blue (about 15 minutes). Then, the mixture was cooled to room temperature, and the solids were separated by filtration. Both solids and filtrate was analyzed by HPLC. The results are shown in Table 1.

TABLE 1

| Example | Additive | Glyphosate Yield(%) | Conversion % | Selectivity % |
|---|---|---|---|---|
| 1 | No additive | 50.8 | 98.8 | 51.4 |
| 2 | diquat* dibromide | 79.2 | 98.8 | 80.2 |
| 3 | 4,4'-bipyridine | 69.0 | 100 | 69.2 |
| 4 | paraquat** dichloride | 68.9 | 98.2 | 70.2 |
| 5 | 1,10-phenanthroline ethylene bromide | 67.1 | 77.7 | 86.4 |

*diquat is N,N'-ethylene-2,2'-dipyridylium
**paraquat is 1,1'-dimethyl-4,4'-bipyridinium

EXAMPLES 6-10

The procedures of Example 2 was repeated except that the mole equivalents of hydrogen peroxide to the mole equivalents of N-phosphonomethyliminodiacetic acid was varied. The results are shown in Table 2.

TABLE 2

| Example | Peroxide Equivalents | Glyphosate Yield(%) | Conversion (%) | Selectivity (%) |
|---|---|---|---|---|
| 6 | 2.6 | 79.2 | 98.8 | 80.2 |
| 7 | 2.4 | 82.9 | 97.4 | 85.1 |
| 8 | 2.2 | 83.0 | 96.9 | 85.7 |
| 9 | 1.5 | 67.0 | 71.2 | 94.1 |
| 10 | 1.1 | 53.0 | 54.2 | 97.8 |

These results show that decreasing the hydrogen peroxide charge from 2.6 mole equivalents to 2.2 mole equivalents increased the yield to 83.0%, and decreasing the peroxide charge to less than two mole equivalents gave higher selectivity, but poorer conversion.

EXAMPLES 11-12

Into a 100 ml round bottomed flask was charged N-phosphonomethyliminodiacetic acid (13,5 g, 0.06 mol), cobalt sulfate (1.7 g), water (50 g) and N,N'-ethylene2,2'dipyridylium dibromide (1.7 g, 0.003 mol.). The mixture was heated to 80° C. and 30% hydrogen peroxide was added dropwise over a 30 minute period. The mixture was then heated to 95° C. for 1.5 hours. The results are shown on Table 3.

TABLE 3

| Example | Additive | Glyphosate Yield(%) | Conversion (%) | Selectivity (%) |
|---|---|---|---|---|
| 11 | No additive | 37.7 | 99.5 | 37.9 |
| 12 | Diquat dibromide | 66.2 | 76.2 | 86.9 |

Although the invention has been described in terms of specified embodiments, which are set forth in considerable detail, it should be understood that this by way of illustration only, and that alternative embodiments and operating techniques will become apparent to those skilled in the art in view of the disclosure. For example, there are numerous dipyridyl compounds known to those skilled in the art that have different substituents rather than alkyl. For example, there are compounds such as 1,1-Diβ-hydroxyethyl-4,4'-bipyridylium dibromide, 1,1'-Diβ-carboxyethyl-4,4'-bipyridylium dichloride, 1,1'-Ethylene-5,5'-dimethyl-2,2'-bipyridylium dibromide, 1,1'-Ethylene-4,4'-dimethyl-2,2'-bipyridylium dibromide, and 1,1'-Trimethylene-2,2'-bipyridylium dibromide. Such compounds may be substituted for the dipyridyl compounds of the present invention provided that the substituents do not cause a deleterious effect on the selectivity to N-phosphonomethylglycine. Accordingly, modifications can be made without departing from the spirit of the described invention.

What is claimed is:

1. A process for the production of N-phosphonomethylglycine comprising contacting N-phosphonomethyliminodiacetic acid with a peroxide in the presence of a catalyst selected from the group consisting of the salts and salt complexes of cobalt and vanadium, and an effective amount of a dipyridyl compound represented by the formula:

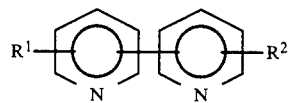
(I)

wherein R¹ and R² are independently selected from the group consisting of hydrogen, alkyl having from one to about 18 carbon atoms, ortho-phenylene, oxygen, sulfur, SO₂, SO₃, N—R⁵ wherein R⁵ is alkyl having from one to six carbon atoms and R¹ and R² together can form a bridge with groups selected from alkylene having from one to about six carbon atoms wherein the alkylene bridge can contain branching or double bonds; or salts thereof represented by the formula

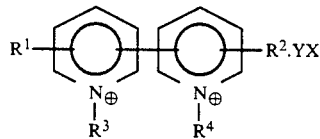
(II)

wherein R¹ and R² are as defined above, Y is one or two depending on whether X is a dianion or a monoanion, and X is selected from the group consisting of halide, sulfate, nitrate, phosphate, and perchlorate; and R³ and R⁴ are individually selected from the group consisting of hydrogen or alkyl having from one to about 18 carbon atoms, and R³ and R⁴ together can form a bridge with groups selected from alkylene having from one to about six carbon atoms wherein the alkylene bridge can contain branching or double bonds.

2. A process of claim 1 wherein the dipyridyl compound concentration is at least 0.0002 molar.

3. A process of claim 2 wherein the catalyst salt concentration is between 0.1 molar and 0.001 molar total metal ion concentration.

4. A process of claim 1 wherein X is bromide.

5. A process of claim 1 wherein the peroxide is hydrogen peroxide.

6. A process of claim 1 wherein the dipyridyl compound is a 4,4'-dipyridyl compound represented by the formula:

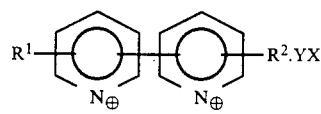

7. A process of claim 6 wherein R₁ and R² are each methyl.

8. A process of claim 6 wherein X is bromide and Y is 2.

9. A process of claim 6 wherein the catalyst is a vanadium salt.

10. A process of claim 6 wherein the catalyst is a cobalt salt.

11. A process of claim 1 wherein R³ and R⁴ together are selected from an alkylene chain having from one to six carbon atoms to provide a dipyridyl compound represented by the formula:

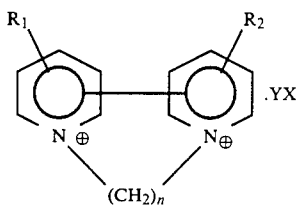

wherein Y is 2, X is chloride or bromide and n is between 1 and 6.

12. A process of claim 11 wherein n is 2.

13. A process of claim 12 wherein X is bromide.

14. A process of claim 11 wherein the dipyridyl compound concentration is at least 0.01 molar.

15. A process of claim 14 wherein the catalyst salt concentration is between 0.1 molar and 0.5 molar total metal concentration.

16. A process of claim 15 wherein the catalyst is a cobalt salt.

17. A process of claim 15 wherein the catalyst is a vanadium salt.

* * * * *